(12) United States Patent
Bay

(10) Patent No.: US 9,833,193 B2
(45) Date of Patent: Dec. 5, 2017

(54) MONITORING DEVICE

(71) Applicant: BIOTELEMETRY TECHNOLOGY APS, Hellerup (DK)

(72) Inventor: Lasse Bay, Copenhagen NV (DK)

(73) Assignee: BIOTELEMETRY TECHNOLOGY APS, Hellerup (DK)

( * ) Notice: Subject to any disclaimer, the term of this patent is extended or adjusted under 35 U.S.C. 154(b) by 232 days.

(21) Appl. No.: 14/435,377

(22) PCT Filed: Oct. 11, 2013

(86) PCT No.: PCT/EP2013/071266
§ 371 (c)(1),
(2) Date: Apr. 13, 2015

(87) PCT Pub. No.: WO2014/057083
PCT Pub. Date: Apr. 17, 2014

(65) Prior Publication Data
US 2015/0250422 A1 Sep. 10, 2015

Related U.S. Application Data

(60) Provisional application No. 61/713,128, filed on Oct. 12, 2012.

(30) Foreign Application Priority Data

Oct. 12, 2012 (DK) .................................. 2012 70625

(51) Int. Cl.
*A61B 5/0408* (2006.01)
*A61B 5/0492* (2006.01)
(Continued)

(52) U.S. Cl.
CPC .............. *A61B 5/6832* (2013.01); *A61B 5/04* (2013.01); *A61B 5/0408* (2013.01);
(Continued)

(58) Field of Classification Search
CPC ... A61B 5/0408; A61B 5/0492; A61B 5/0533; A61B 5/6832
(Continued)

(56) References Cited

U.S. PATENT DOCUMENTS 5,054,488 A 10/1991 Muz
6,032,064 A * 2/2000 Devlin ............... A61B 5/04004
600/372

(Continued)

FOREIGN PATENT DOCUMENTS

CN 200966617 Y 10/2007
CN 101237815 A 8/2008
(Continued)

OTHER PUBLICATIONS

International Search Report for PCT/EP2013/071266, Completed by the European Patent Office dated Feb. 6, 2014, 5 Pages.
(Continued)

*Primary Examiner* — Lee S Cohen
(74) *Attorney, Agent, or Firm* — Ropes & Gray LLP

(57) ABSTRACT

A monitoring device suitable for attachment to a surface of a subject, the device having a data collector and a processor. The data collector includes a flexible foil attached to a less flexible socket, where the foil forms a dermal side surface of the data collector for adhesion to a skin surface of a subject to be monitored. To enable communication of electrical signals between the data collector and the processor, the data collector includes a distribution structure formed as a pattern of an electrically conductive material on an outer surface of a foldable sheet. The foldable sheet forms a layer in the flexible foil and having an interface portion which is folded into an aperture in the socket to form a coupling inside the
(Continued)

cavity for electrical communication with a matching coupling of the processor when the processor is received in the cavity.

15 Claims, 8 Drawing Sheets

(51) Int. Cl.

| | | |
|---|---|---|
| *A61B 5/00* | (2006.01) | |
| *A61B 5/04* | (2006.01) | |
| *A61B 5/0476* | (2006.01) | |
| *A61B 5/0488* | (2006.01) | |
| *A61B 5/053* | (2006.01) | |
| *A61B 5/0432* | (2006.01) | |
| *A61B 5/08* | (2006.01) | |

(52) U.S. Cl.
CPC ........ *A61B 5/0476* (2013.01); *A61B 5/04087* (2013.01); *A61B 5/0488* (2013.01); *A61B 5/0492* (2013.01); *A61B 5/0533* (2013.01); *A61B 5/6833* (2013.01); *A61B 5/0432* (2013.01); *A61B 5/0816* (2013.01); *A61B 2560/0209* (2013.01); *A61B 2562/125* (2013.01); *Y10T 29/49151* (2015.01)

(58) Field of Classification Search
USPC ................................ 600/391–393, 509, 547
See application file for complete search history.

(56) References Cited

U.S. PATENT DOCUMENTS

| | | | |
|---|---|---|---|
| 8,870,857 B2 * | 10/2014 | Seymour .............. | A61B 5/0084 600/342 |
| 2006/0183984 A1 | 8/2006 | Dobbles et al. | |
| 2008/0288026 A1 | 11/2008 | Cross et al. | |
| 2012/0089037 A1 | 4/2012 | Bishay et al. | |
| 2012/0101349 A1 | 4/2012 | Dellostritto et al. | |

FOREIGN PATENT DOCUMENTS

| | | |
|---|---|---|
| CN | 102138860 A | 8/2011 |
| CN | 202207144 U | 5/2012 |
| WO | 03065926 | 8/2003 |
| WO | 2006094513 | 9/2006 |
| WO | 2011076871 | 6/2011 |

OTHER PUBLICATIONS

Danish Search Report for Application No. 2012 70625, Completed by the Danish Patent and Trademark Office dated May 27, 2013, 1 Page.
Website http://www.axelgaard.com/home.htm Retrieved from the Wayback Machine on Jul. 27, 2015, Dated Sep. 27, 2012, 2 Pages, "AXELGAARD Manufacturing co., LTD, Electrodes and Hydrogels.".
Website http://www.amgel.com/index.html Retrieved from the Wayback Machine on Jul. 27, 2015, Dated Jan. 20, 2012, 1 Page, "AmGel Technologies".

\* cited by examiner

MONITORING DEVICE

CROSS-REFERENCE TO RELATED APPLICATION

This application is the U.S. national phase of PCT Application No. PCT/EP2013/071266 filed on Oct. 11, 2013, which claims priority to DK Patent Application No. PA201270625 filed on Oct. 12, 2012, and the benefit to U.S. Provisional Application No. 61/713,128 filed Oct. 12, 2012, the disclosures of which are incorporated in their entirety by reference herein.

Data logging and monitoring of physiological signals are widely used, e.g. for sports training and for medical purposes, e.g. for surveillance of critical physiological parameters detectable e.g. from electrical signals generated in the body, skin or blood color, temperature, light absorbance etc.

The present invention relates to a monitoring device for monitoring a subject. Particularly, the invention relates to a device comprising a data collector and a separate processor. The data collector is adapted for adhesive attachment to a body surface.

BACKGROUND OF THE INVENTION

One group of existing monitoring devices comprises a patch which is attachable to a skin surface and which includes a processor and/or a transmitter for transmitting a captured body signal in raw or processed form. Such monitoring devices are known e.g. for sport training purposes where they are integrated in a belt to be fastened over the chest, about the wrist or at other body locations. Typically, they are used repeatedly by the same user.

Another group of existing devices comprises a patch working as a sensor or data collector and a separate processor which can process the collected data. The patch and processor are typically joined adhesively or by a kind of snap-locking feature. Due to the two-part structure with a separate processor, the known devices often become bulky and heavy, and they are typically not comfortable to wear, or they are difficult to fit onto the body. As an example, it is not unusual that cloth, hair and other items become trapped between the data collector and the processor, that data exchange between the data collector and the processor fails, or that the data collector and processor separates unintentionally.

WO 2006094513 discloses a micro electronic system predominantly for monitoring physiological or neurological conditions. The system is embedded in a three-dimensional adhesive device which can be attached to the skin of a mammal. The microelectronic system uses wireless communication and it is useful for measuring ECG (Electro CardioGraphy), EMG (Electro MyoGraphy), EEG (Electro EncephaloGraphy), blood glucose, pulse, blood pressure, pH, and oxygen.

WO 03/065926 discloses a wearable biomonitor with a flexible and thin integrated circuit. The disclosure includes ways to achieve high comfort of wear by using a thin layer adhesive or pads of adhesive for fixation to the skin.

U.S. Pat. No. 5,054,488 discloses an opto-electronic sensor for producing electrical signals representative of a physiological condition. The sensors may be attached to the body by a double-sided pressure sensitive adhesive on a polyester lining.

SUMMARY OF THE INVENTION

It is an object of embodiments of the invention to provide a device with a two-part structure which, in spite of being in two parts, is easy to use, comfortable to wear, and which minimizes the risk of getting entangled with items during use, and generally performs better than the known devices.

According to a first aspect, the invention provides a monitoring device comprising a data collector and a separate processor, the data collector comprising a flexible foil attached to a less flexible socket, the foil forming a dermal side surface for adhesion of the data collector to a skin surface of a subject to be monitored and the socket forming a cavity for receiving the processor, wherein the data collector further comprises a foldable sheet with a first pattern of an electrically conductive material on an outer surface thereof, the first pattern extending between a sensing portion of the sheet which forms a layer in the flexible foil and an interface portion of the sheet which is folded into an aperture in the socket and forms an electrical coupling for electrically connecting the processor to the data collector.

The foldable sheet enables a very thin conductor facilitating electrical communication between the processor and the data collector. This enables a very low height of the device over the skin surface of the subject. Due to the combination between the flexible foil in which the foldable sheet is integrated, and the more rigid structure of the socket, good communication can be ensured even with a flexible foil and sheet structure. Accordingly, the invention facilitates a solid device with a low height and good electrical connectivity. Since the foldable sheet forms a layer in the flexible foil, the foil itself becomes an electrical conductor which saves material and thus both weight and height, and which simultaneously can reduce the manufacturing costs.

Particularly, the folded sheet may be a continuous single sheet element which is folded.

The main function of the data collector may e.g. be to adhere to the body of the subject, to recognize physiologic signals there from, and to transmit the monitoring signals which represents the physiologic signal to the processor. The monitoring signal may be the physiologic signal itself or the data collector may comprise a transducer for converting a physiological signal into another form, typically a form which is easier to transfer to the processor and/or a form which is more easily processed by the processor. As it will be described in further details in a separate paragraph, the transducer may form part of the data collector, the processor or both.

Examples of physiological signals relevant in connection with the invention include (ECG), electromyography (EMG) electroencephalography (EEG), galvanic skin response (GSR), photoplethysmography (PPG), phonocardiogram (PCG), arterial oxygen saturation (Sp02), muscle activity, emotions, arterial saturation of carbon monoxide (SpCO) and blood carbon dioxide (CO2), blood pressure (BP), respiration, such as respiration frequency (RF) and/or respiration volume (RV), heart rate (HR), pulse, bioimpedance, and/or rhythm, heart sounds, respiratory sounds, blood pressure, posture, wake/sleep, orthopnea, heat flux, patient activity, snoring sound or other sounds of the subject, and temperature, such as skin temperature (ST), and/or core body temperature.

Such signals may be significant for a physiological condition of the subject and in particular for vital parameters where failure will lead to death.

The data collector includes the two main components, i.e. the foil and the socket. The foil may be made from a flexible tape or patch with an adhesive on at least the dermal side surface.

Herein, the dermal side surface is, by definition, that surface of the data collector which is for adhesive attachment to the skin surface of the monitored subject. Also by definition, the dermal side of the entire device or of individual structural entities in the device is that side of the device or structural entity facing towards the skin surface when the device is attached to a subject.

The dermal side surface may comprise a pressure sensitive adhesive (PSA) for adhesive attachment of the device to the body. In one embodiment, the dermal side surface comprises a gel, e.g. a hydrogel with adhesive properties. The hydrogel may or may not be electrically conductive. Different forms or formulations of the hydrogel with different properties may be used within the same system or device.

Examples of suitable hydrogels may be obtained from Axelgaard Manufacturing Co., Ltd: http://www.axelgaard.com/home.htm or its subdivision AmGel Technologies; http://www.amgel.com/index.html.

The adhesive or gel may form a transmission passage for the physiological signal from the subject on which the device is attached.

In particular, it may be an advantage to use an adhesive, e.g. in form of a hydrogel or similar material with properties ranging from soft and weak jelly-like ranging up to hard and tough yet deformable, and it may further be an advantage to use a material with a refractive index in the range of 1.01-1.7 e.g. 1.30-1.45, such as 1.34-1.42. In this way, the index becomes close to that of average skin whereby reflection of the physiological signal, be that an acoustic or optic signal, can be prevented or at least reduced.

Herein, flexibility of the foil means that the foil can bend to a certain degree, i.e. it can follow the contour of the body. The foil may, additionally, be lengthwise elastically deformable such that it can be stretched, e.g. to follow stretching of body parts.

The foil, and particularly the foldable sheet could be made of non-conductive material. Herein, non-conductive should be understood as having an electrical conductivity much lower than that of the conductive pattern(s), e.g. having a resistivity twice that of the conductive pattern or 4 times that of the conductive pattern or more than 10 times that of the conductive pattern.

The socket is less flexible and it is rigidly connected to the foil, e.g. by a strong adhesive preventing the removal of the socket from the foil. The socket may have a bottom following the surface of the foil, and sidewalls extending upwardly from the bottom and forming a flange about an opening in which the processor is received.

The sensing portion of the foldable sheet is integral with the foil, i.e. it forms one of the layers in the foil, and it is therefore held in a plane defined by the foil. Herein, the definition of the interface portion being "folded into an aperture in the socket" means that the interface portion is bend, or turned over, or in any other way is deformed out of the plane of the foil and into the cavity via an opening in the socket. The interface and sensing portions are therefore one and the same sheet, and due to the foldability, this sheet may both be integrated in the foil and it may extend into the cavity where it forms a coupling for electrical communication with the processor.

The first pattern is printed on the same surface, specified as "an outer surface" of the foldable sheet. Depending on the way the foldable sheet is located in the foil structure, the outer surface becomes in a direction towards the dermal side surface of the data collector or in the opposite direction away from the dermal side surface. Depending on the way the interface portion is folded into the aperture of the socket, the outer surface of the interface portion of the sheet faces away from the outer surface of the sensing portion, or it faces in the same direction as the outer surface of the interface portion, i.e. the outer surface and thus the first pattern of the interface portion may face towards the dermal side surface or opposite the dermal side surface, which is typically towards the processor.

The processor comprises a computer unit e.g. for processing a physiological signal which is received from the individual. Additionally, the processor may comprise a battery, computer memory, a display and other features, e.g. for enabling communication with external devices, e.g. wireless communication features etc.

In some embodiments in the system according to the present invention the device comprises at least one sensor and optionally several different sensors. The sensor(s) may be configured for measuring one or more physiological signal selected from electrocardiography (ECG), electromyography (EMG) electroencephalography (EEG), galvanic skin response (GSR), phonocardiogram (PCG), arterial oxygen saturation (Sp02), muscle activity, emotions, arterial saturation of carbon monoxide (SpCO) and blood carbon dioxide (CO2), blood pressure (BP), respiration, such as respiration frequency (RF) and/or respiration volume (RV), heart rate (HR), pulse, bioimpedance, and/or rhythm, heart sounds, respiratory sounds, blood pressure, posture, wake/sleep, orthopnea, heat flux, patient activity, snoring sound or other sounds of the subject, and temperature, such as skin temperature (ST), and/or core body temperature.

In general, the physiological signal will be recognized and picked up from the individual by a structure which in the following will be referred to as "the detecting component". This component can e.g. include electrodes (polar, bipolar), pressure sensors, needles with electrodes, accelerometers, photo detectors, microphones, ion specific field effect transistors (ISFET), a NTC (negative temperature coefficient) resistors, band gap detectors, ion membranes, enzyme reactors or condensers etc. In particular, the device may comprise components for non-invasive capturing of the physiological signal, e.g. electrodes or optic recognition means. The component could, however, also be for invasive capturing of the physiological signal, e.g. in the form of a needle for taking fluid samples, or a needle containing an electrode for subcutaneous capturing of an electrical physiological signal.

Accordingly, the data collector may further comprise at least one electrode for communicating an electrical signal between the monitoring device and the subject, e.g. for capturing an electrical activity produced by the subject. The first pattern may be electrically connected to the electrode and thereby provide individual conductivity between each electrode and the coupling inside the cavity of the socket.

The at least one electrode may comprise a second pattern of electrically conductive material on the outer surface of a sensing portion of the foldable sheet. The second pattern and the first pattern could be of identical electrically conductive material.

Since both the second pattern and the first pattern are provided on the outer surface of the foldable sheet, i.e. on the same surface of the foldable sheet, it becomes very easy to produce the data collector.

In summary, it can be produced by printing the first and second patterns on one side of a foldable sheet, integrating a sensing portion of the sheet in a laminated foil structure, and bending an interface portion of the sheet through an aperture in the socket. The result is potentially a very flat, cheap, and reliable structure with a low weight and a high strength, e.g. as a result of a laminated structure of the foil, and as a result of the rigid and less flexible structure of the socket.

Due to the foldability of the sheet which carries the first, and optionally also the second pattern, the quality of the connection between the sheet and the processor may suffer, i.e. the sheet may become deformed by folding whereby the connectivity can be lost. This can be remedied by receiving the interface portion of the foldable sheet in a plug structure which is rigid and which can be received in a matching socket in the processor. This, however, may increase the thickness, weight, and costs of the device. To provide a slim, cheap, and good electrical connectivity, the interface portion of the foldable sheet may, itself, form the coupling in the cavity—i.e. the coupling may be constituted by the interface portion. To increase the quality of the connection, it may be desirable to arrange the socket, which is less flexible than the foil, between the interface portion and the sensing portion of the sheet accordingly, the processor can be pressed against the interface portion of the foldable sheet and the socket may form a rigid backing behind the foldable sheet and thus ensure connectivity.

To further increase the good connectivity between the interface portion of the foldable sheet and the processor, the device may comprise a spring structure which presses the interface portion towards the coupling of the processor.

Particularly, the spring structure may form an integrated part of the socket, and may be located between the interface portion of the sheet and the dermal side surface of the data collector.

The aforementioned pressing of the interface portion towards the processor may be provided by an upwards spring force, i.e. a spring force in a direction from the coupling of the socket towards the processor', perpendicular to and directed away from the dermal side surface.

The processor may particularly be receivable into the cavity in a downwards direction being perpendicularly to and directed towards the dermal side surface, i.e. opposite the aforementioned upwards direction.

Alternatively, the processor may be receivable into the cavity in a sideways direction being parallel to and directed towards the dermal side surface.

To further increase the simplicity, to reduce the weight and costs, and to increase the durability of the device, the spring structure may comprise a number of upwards protrusions separated from adjacent protrusions by a recess or opening in the socket. Particularly, such protrusions may be formed in one part with the remaining parts of the socket, i.e. it may be made from the same material, e.g. molded in one piece. The protrusions may e.g. project in the aforementioned upwards direction relative to the bottom of the socket.

The recesses or openings between adjacent protrusions could be oblong and extend in a direction being parallel to the sideways direction. This facilitates sliding of the processor in contact with the coupling, and thereby facilitates the sideways insertion of the processor into the cavity.

The socket may form a locking structure adapted to hold the processor in the cavity. Particularly, the socket may form a locking structure for snap-locking of the processor, i.e. automatically engaging the processor when the processor is inserted in the cavity. The locking structure may be for releasable locking of the processor, and particularly, the locking structure may be adapted for controlled destruction for removal of the processor. This ensures one-time use of the data collector, particularly, when the controlled destruction is such that renewed insertion of the processor is prevented or at least such that the processor is no longer capable of being fixed in the cavity.

The locking structure may apply a constant force on the processor in a downwards direction being perpendicularly to and directed towards the dermal side surface thereby forcing the processor into the cavity. The locking structure thereby presses the processor against the force of the aforementioned springs, and a good electrical contact between the data collector and the processor can be established.

In a second aspect, the invention provides a monitoring device comprising a data collector and a separate processor, the data collector comprising a flexible foil attached to a less flexible socket, the foil forming a dermal side surface for adhesion of the data collector to a skin surface of a subject to be monitored and the socket forming a cavity for receiving the processor, wherein the processor comprises a connector for establishing a cabled connection to an external unit, the connector being covered by the socket, when the processor is received in the cavity.

According to this aspect of the invention, the socket prevents access to the connector and the user is therefore prevented from establishing cabled connections to external units when the processor is in the socket. Since the computer would typically be in the socket when the device is attached to the body of the user, the invention according to the second aspect prevents cabled connection to the processor when the device is attached to the body of the user, and this reduces the risk of malfunctioning and the potential risk of causing electrical shock if a connected external unit has a malfunction. Accordingly, the invention according to the second aspect increases the safety in using a device according to the first aspect of the invention.

The connector could e.g. be a mini USB connector or any similar kind of standardized connector, e.g. for connection of the processor to an external computer, battery charger, or other external equipment.

In a third aspect, the invention provides monitoring device comprising a data collector and a separate processor, the data collector comprising a flexible foil attached to a less flexible socket, the foil forming a dermal side surface for adhesion of the data collector to a skin surface of a subject to be monitored and the socket forming a cavity for receiving the processor, wherein the processor and the socket have matching shapes facilitating the processor to be received in the cavity only in one single orientation of the processor relative to the socket.

By "matching shape", is herein considered the shape of the contour of that edge of the processor which is received in the cavity, and the corresponding shape of that edge of the cavity in which the processor is received. For simplicity, this will be referred to herein as "the interface".

As an example, the interface should not be circular, oval, quadrangular, or isosceles triangular. In a more general definition, the shape should be such that at most one line of symmetry, i.e. a line along which the shape of the interface becomes symmetric or mirrored across the line, can be established. If two or more of such lines of symmetry can be established for the interface, then the processor would be receivable in the cavity in two or more different orientations depending on the number of lines of symmetry. The purpose of the invention according to the third aspect is to avoid such multiple possibilities of orientation and thereby ensure correct attachment of the processor in the socket. The invention according to the third aspect of the invention therefore increases the correctness of use and facilitates less faulty attachments.

The devices according to the second and third aspects of the invention may comprise any of the features mentioned relative to the device according to the first aspect of the invention.

In a fourth aspect, the invention provides a method of making a device according to the first aspect of the invention. The method comprises the steps of:
- providing an interface pattern of an electrically conductive material on an outer surface of a foldable sheet;
- providing a flexible foil which includes the foldable sheet and which forms a dermal side surface for adhesive contact with a skin surface;
- providing a socket which is less flexible than the foil;
- attaching the socket to an upper surface of the foil facing away from the dermal side surface; and
- folding an interface portion of the sheet through an aperture in the socket; and
- providing from the interface portion, a coupling for electrical communication with a matching coupling of the processor.

In one embodiment, the steps are carried out in the order mentioned above.

The method may comprise the step of providing a sensing pattern of the electrically conductive material to the outer surface of a sensing portion of the sheet, and arranging the sensing portion such that the sensing and interface portions are on opposite sides of the socket.

The method may comprise the step of providing a spring structure in the socket between the sensing and interface portions of the sheet.

Generally, the method according to the fourth aspect of the invention may comprise any step for providing a device according to any of the first, second, and third aspects and/or for using a device according to the first, second, or third aspects of the invention.

LIST OF DRAWINGS

In the following, embodiments of the invention will be described by way of example with reference to the figures in which.

Further scope of applicability of the present invention will become apparent from the following detailed description and specific examples. However, it should be understood that the detailed description and specific examples, while indicating preferred embodiments of the invention, are given by way of illustration only, since various changes and modifications within the scope of the invention will become apparent to those skilled in the art from this detailed description.

DETAILED DESCRIPTION OF DRAWINGS

Figure 1:
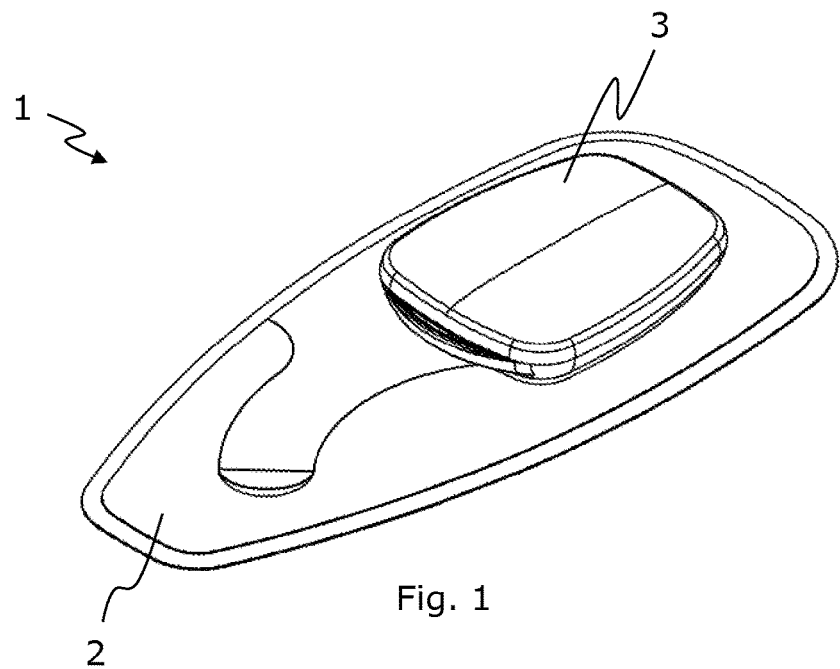
FIGS. 1 and 2 illustrate a monitoring device according to the invention.
Figure 2:
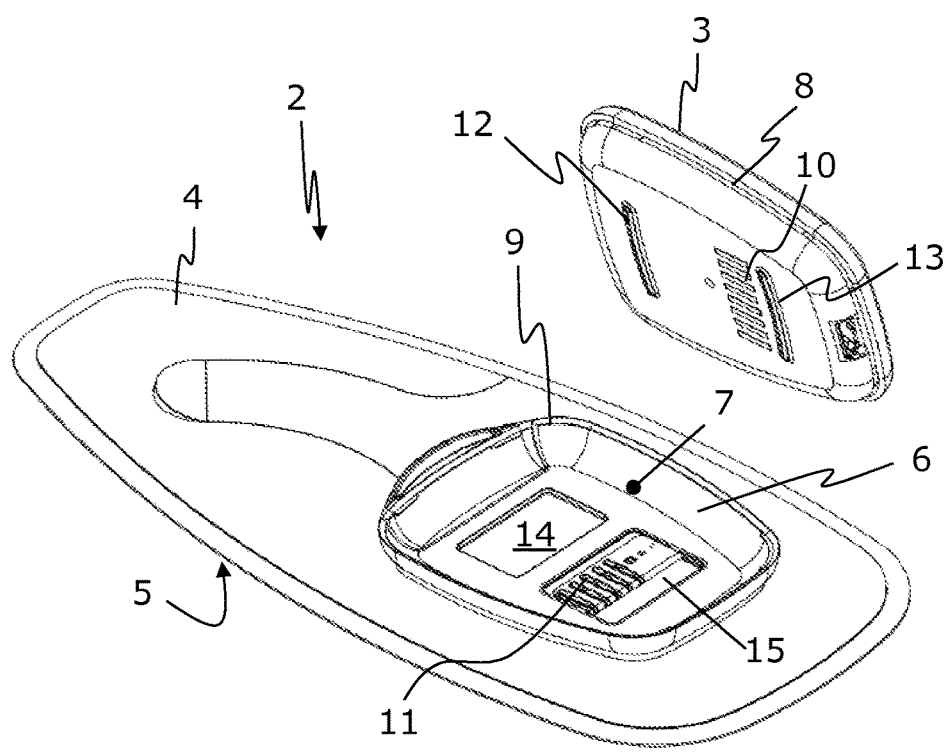

FIGS. 1 and 2 illustrate a monitoring device 1 comprising a data collector 2 and a separate processor 3 which is detachably attachable to the data collector. In FIG. 1, the processor is attached to the data collector, and in FIG. 2, the processor is detached from the data collector.

The data collector comprises a flexible foil 4 made from an elastically or at least flexible material. On a dermal side surface 5, the foil comprises an adhesive, e.g. a hydrocolloid adhesive for adhesion of the data collector to a skin surface of a subject to be monitored. On an opposite, upper surface of the foil, the data collector comprises a socket 6 made from a rigid plastic material and being less flexible than the foil. The socket and the foil are adhesively, and preferably, non-detachably joined. The flexibility of the foil enables the foil to be adhesively attached to the skin surface and to follow the contour of the body. The foil may, additionally, be lengthwise elastically deformable such that it can be stretched. The foil has a laminated structure including numerous thin layers of different materials.

The socket forms a cavity 7 for receiving the processor. The cavity has a depth of approximately half of the height of the processor, i.e. such that half of the processor may be depressed into the cavity. The processor includes a shoulder 8 which comes in contact with the upper edge 9 of the socket. At this point, the electrical coupling 10 of the processor and the electrical coupling 11 of the data collector are joined, and electrical communication between the data collector and the processor is established.

To reduce impact of moisture, water, or dirt etc., the socket and/or the processor may include a resilient, elastically deformable, gasket located between the socket and the processor and which is compressed when the processor is inserted in the socket. The gasket could be located on or at the shoulder 8 or on/at the upper edge 9.

The processor includes a pair of steps 12, 13 which are received in matching windows 14, 15 in the socket. The steps provide a free space under the electrical coupling of the processor, when the processor is placed on a table etc. and thereby protects the electrical terminals against contamination and wear.

Figure 3:
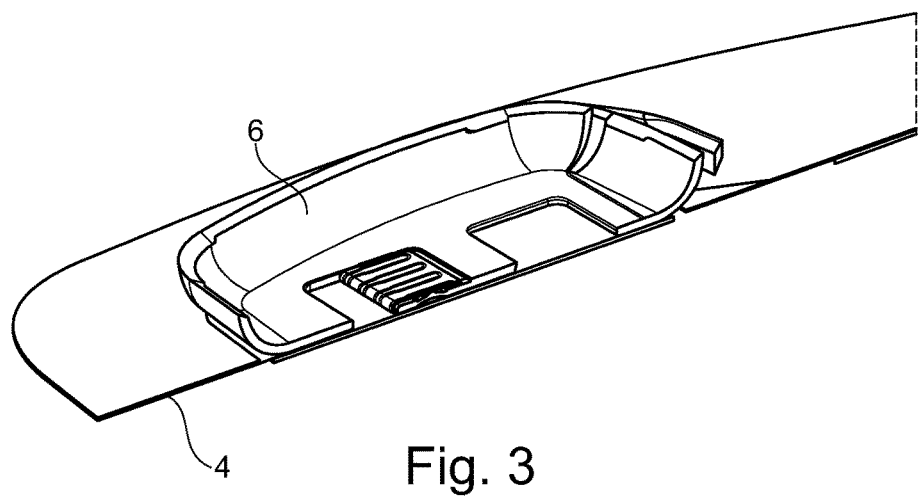
FIGS. 3 and 4 illustrate details of the socket and foil in a cross-sectional view.
Figure 4:
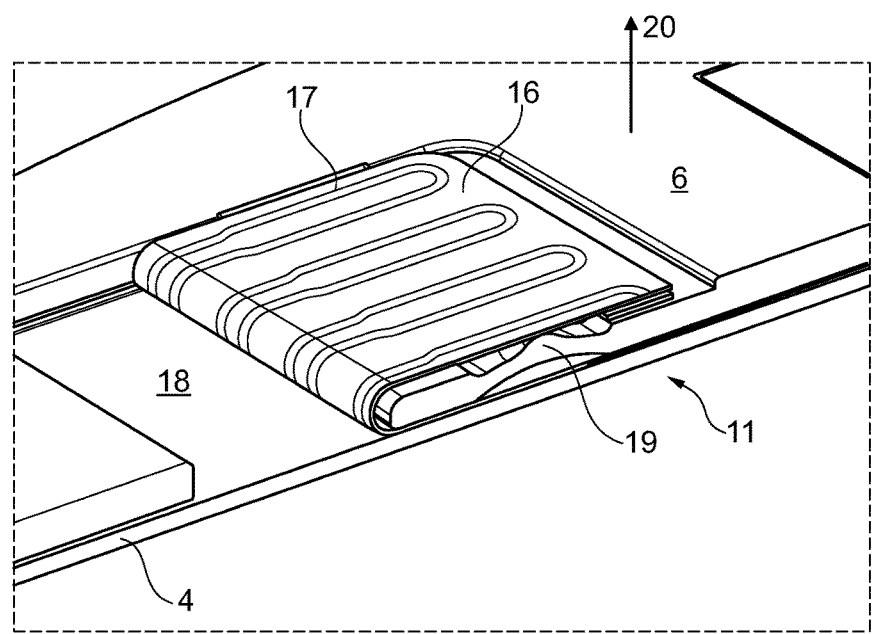

FIG. 3 illustrates a cross sectional view of the data collector and FIG. 4 illustrates details herein, particularly of the electrical coupling 11 of the data collector. The data collector comprises a sheet 16 with a pattern 17 of an electrically conductive material, herein referred to as "a first pattern". The first pattern is printed on an outer surface of the sheet. A portion of the sheet, herein referred to as "a sensing portion" is integrated into the laminated structure of the foil, i.e. it forms one of the layers in the laminated structure. The sheet is foldable, and an interface portion of the sheet is folded through an aperture or window 18 into the cavity. By this folding of the sheet, the outer surface becomes upwards, i.e. it faces towards the processor when the processor is received in the cavity.

Since the first pattern is applied to the outer surface of both the sensing portion and the interface portion, the folded sheet forms a very flat and thin electrical coupling for electrically connecting the processor to the data collector.

FIG. 4 also illustrates an upward protrusion 19 forming a spring structure which provides a spring force in the upwards direction indicated by the arrow 20.

Figure 5:
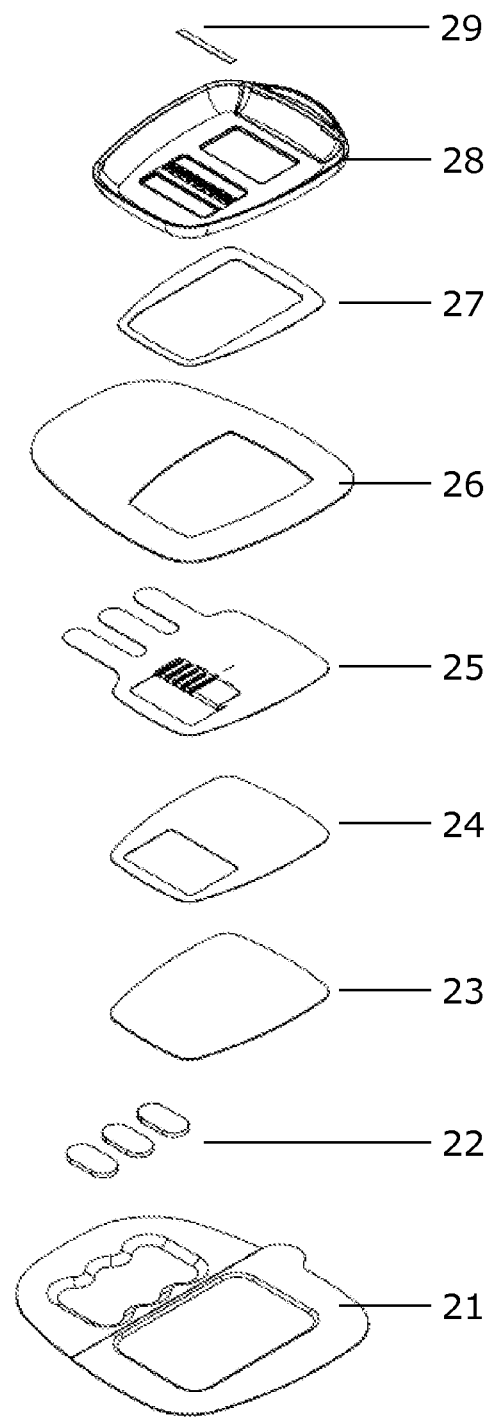
FIG. 5 illustrates the layers in a data collector adapted for EMG signal detection.

FIG. 5 illustrates the data collector in an exploded view, in this case in an embodiment suitable for EMG signal detection. Herein, it is clearly seen that the foil has a laminated structure including a plurality of layers, 21-27, and that the foldable sheet 25 constitutes one of the layers. The more rigid socket has numeral 28.

FIG. 5 illustrates the layers in a data collector adapted for EMG. In this data collector, table 1 below specifies detailed materials suitable for each layer.

TABLE NO 1

| Numeral | Description | Material |
|---------|-------------|----------|
| 25 | Foldable sheet with printed electrical conductors and electrodes, i.e. printed with the first and second patterns of electrically conductive material. | PET (polyester) foil with silver/silver chloride conductive ink |
| 26 | Skin adhesive tape | Acrylic adhesive with PET non-woven backing |
| 24 | Double sided adhesive tape | Acrylate adhesive reinforced with polyester fibers |
| 23 | Skin adhesive tape | Acrylic adhesive with PET non-woven backing |
| 22 | Conductive Sensing Hydrogel | Polyacrylate based hydrogel |
| 27 | Double sided adhesive tape located between the interface portion of the sheet 25 and the socket 28. | Acrylate adhesive reinforced with polyester fibers |
| 29 | Double sided adhesive tape | Acrylate adhesive reinforced with polyester fibers |
| 28 | Injection molded socket | ABS (Acrylonitrile butadiene styrene) |
| 21 | Release liner | Silicone coated PET foil |

Figure 6:
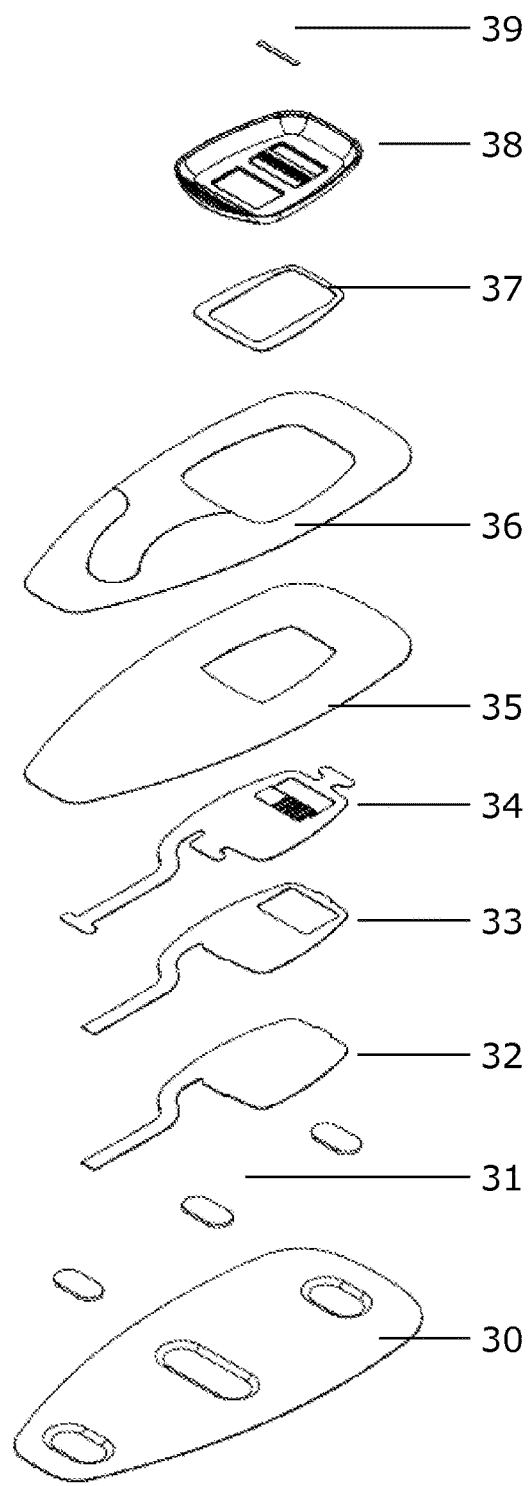
FIG. 6 illustrates an embodiment of the data collector suitable for ECG signal detection.
Figure 7:
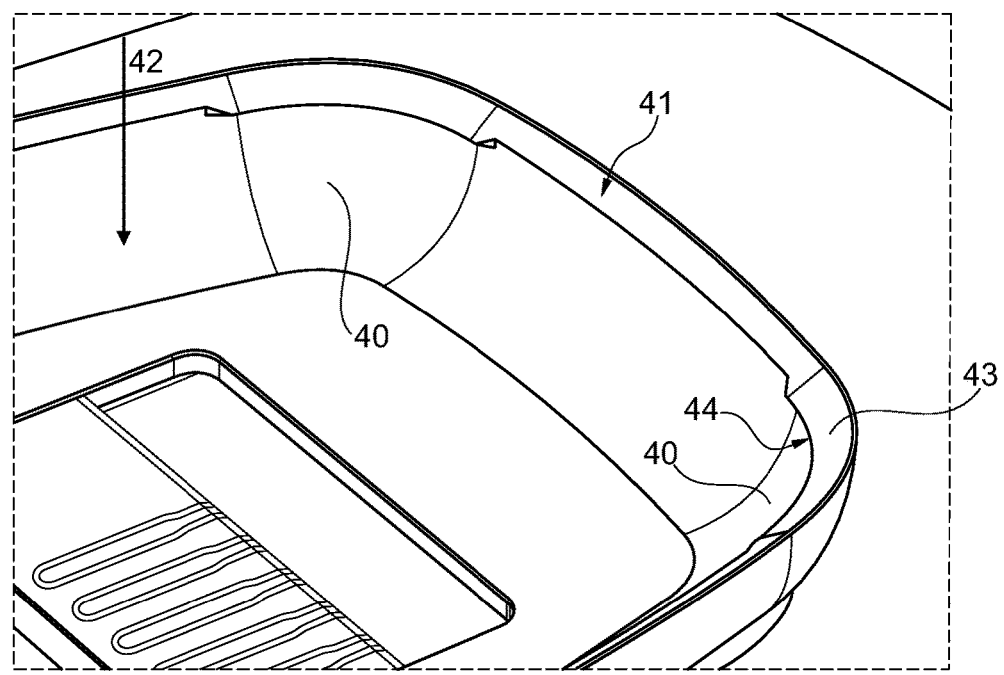
FIGS. 7-10 illustrate details of the locking structure adapted to hold the processor in the cavity.
Figure 8:
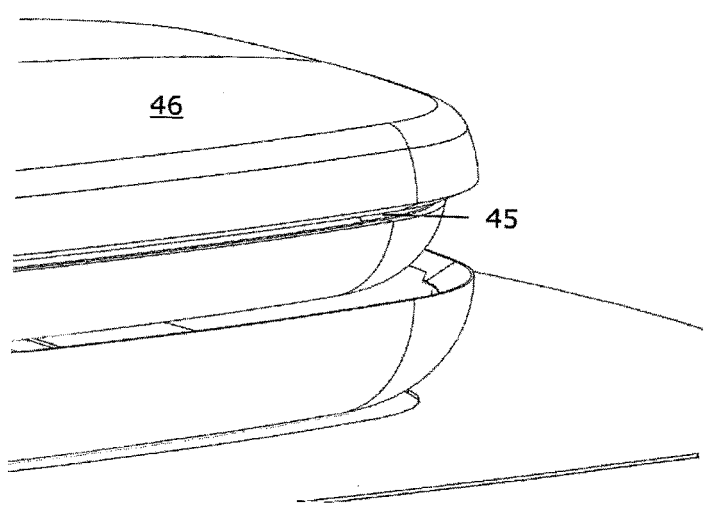

FIG. 6 illustrates an alternative embodiment of the data collector in an exploded view, in this case suitable for ECG signal detection. Again, it is clearly seen that the foil has a laminated structure including a plurality of layers, 30-37, and that the foldable sheet 34 constitutes one of the layers. The more rigid socket has numeral 38.

Table 2 below specifies detailed materials suitable for each layer in the ECG data collector.

TABLE NO. 2

| Numeral | Description | Material |
|---------|-------------|----------|
| 34 | Foldable sheet with printed electrical conductors and electrodes, i.e. printed with the first and second patterns of electrically conductive material | PET (polyester) foil with silver/silver chloride conductive ink |
| 35 | Skin adhesive tape | Acrylic adhesive with PUR (Polyurethane) backing |
| 37 | Double sided adhesive tape | Acrylate adhesive reinforced with polyester fibers |
| 39 | Double sided adhesive tape | Acrylate adhesive reinforced with polyester fibers |
| 32 | Skin adhesive tape | Acrylic adhesive with PET non-woven backing |
| 31 | Conductive Sensing Hydrogel | Polyacrylate based hydrogel |
| 30 | Release liner | Silicone coated PET foil |
| 36 | Carrier for patch | Silicone coated paper |
| 38 | Injection molded socket | ABS (Acrylonitrile butadiene styrene) |
| 33 | Double sided adhesive tape | acrylate adhesive reinforced with polyester fibers |

FIGS. 7-10 illustrate details of the locking structure adapted to hold the processor in the cavity.

The locking structure comprises a number of flexible protrusions 40 arranged sequentially around the upper edge 41 of the socket, i.e. mainly at the corners of the upper edge. Relative to the downwards direction for inserting the processor in the cavity, i.e. the direction indicated by the arrow 42, the protrusions has a beveled upper edge surface 43 and an opposite transverse edge surface 44. Due to the beveled upper edge surface, the depressed edge 45 of the processor 46 can be pressed down in level with the protrusions, whereby the protrusions engage the depressed edge and locks the processor to the socket. Due to the transverse edge surface 44, the processor is fixed and can only be removed by destruction of the socket.

The socket, and particularly the protrusions are arranged and shaped relative to the processor and particularly relative to the depressed edge such that the locking structure applies a constant force on the processor in the downwards direction illustrated by the arrow 42, i.e. directed towards the dermal side surface thereby forcing the processor into the cavity and downwards onto the electrical coupling formed by the interface portion of the foldable sheet.

The socket may form a sealing edge to the processor in the cavity. The sealing edge prevents fluid (e.g. water) from entering the cavity. The sealing characteristics may be obtained by use of the same rigid plastic materials by which the socket and the processor is made, e.g. by use of different angles of the edge surface ensuring sealing. Alternatively, or in combination, a softer material, e.g. rubber or thermoplastic elastomers, may be provided on the edge of the socket or on the processor. The locking structure may apply a constant force on the processor whereby the softer material becomes deformed and sealing is obtained.

Figure 9:
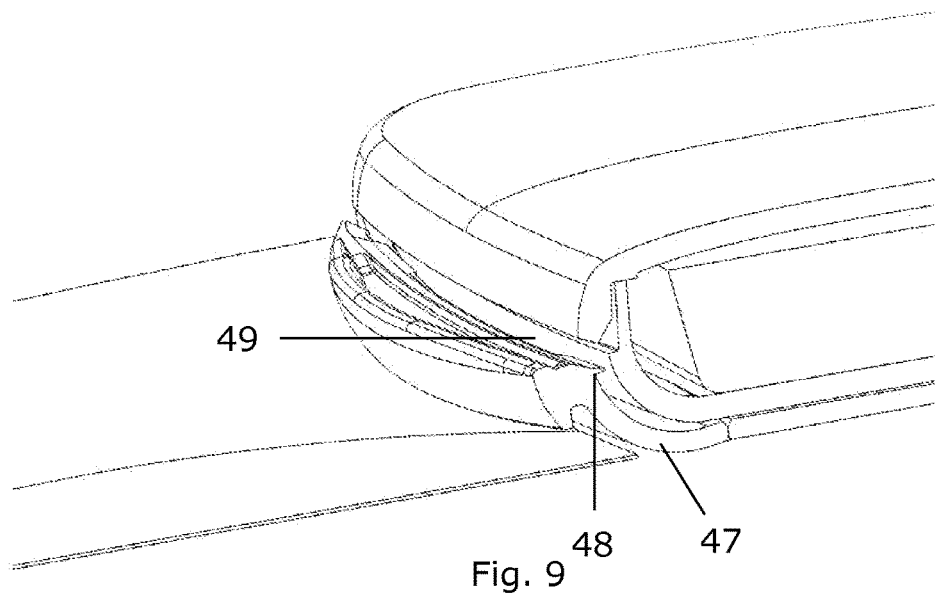
Figure 10:
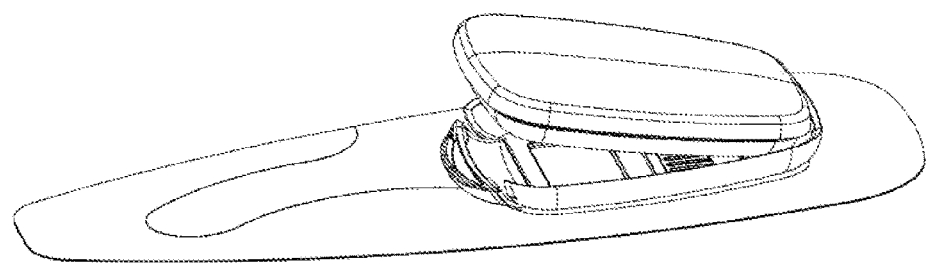

FIG. 9 illustrates an opposite end of the socket in a cross-sectional view. In this vies, it can be seen that the socket is designed for controlled destruction. By breaking an end portion 47 of the socket outwards, the locking protrusions 48 are pulled out of the depressed edge 49 and the processor is released from the socket. FIG. 10 illustrates that the processor can be lifted out of the socket.

Figure 11:
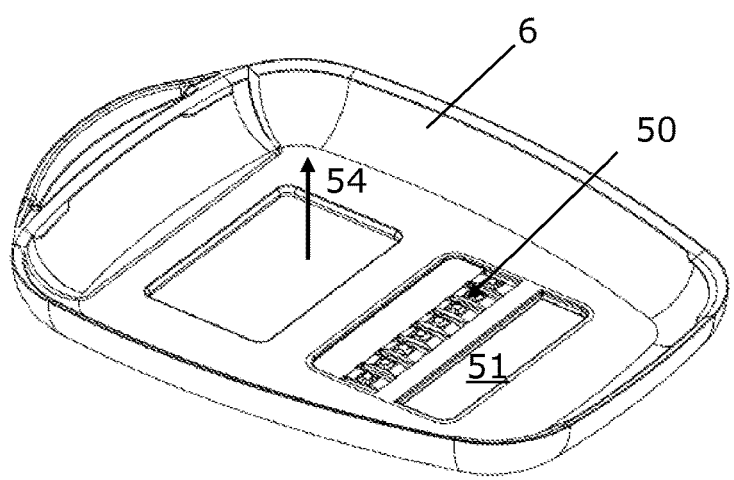
FIGS. 11 and 12 illustrate a socket and details of a spring structure forming part of the socket.
Figure 12:
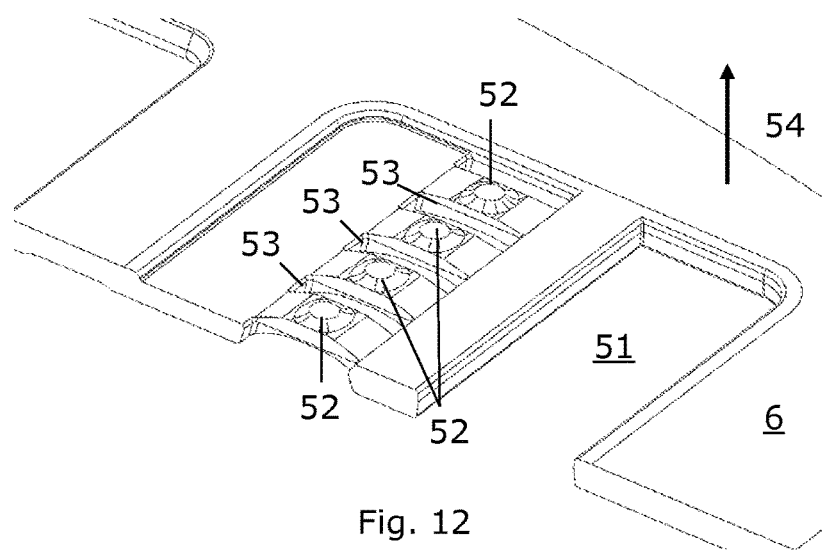

FIGS. 11 and 12 illustrate a socket 6 and details of a spring structure forming part of the socket. In FIGS. 11 and 12, the sheet and the foil in which the sheet forms an integrated layer is omitted to more clearly illustrate the spring structure. The spring structure 50 is located directly adjacent the through opening forming a window 51 through which the interface portion of the sheet is folded. The spring structure comprises a number of upwards protrusions best seen in FIG. 12 and being indicated with numeral 52. The upwards protrusions are separated from adjacent protrusions by through holes forming openings 53 (c.f. FIG. 12) in the socket. The openings are oblong and extend in a direction which herein is referred to as "a sideways direction".

Due to the upwards direction of the protrusions, indicated in FIG. 11 by the arrow 54, the spring structure provides a spring force in an upwards direction when the protrusions are deformed downwardly upon inserting the processor in the cavity. The spring structure forms part of the socket 6, i.e. it is formed in one part with the socket, e.g. by pressure molding or vacuum molding etc. e.g. from a plastic material being more rigid than the sheet and foil.

Figure 13:
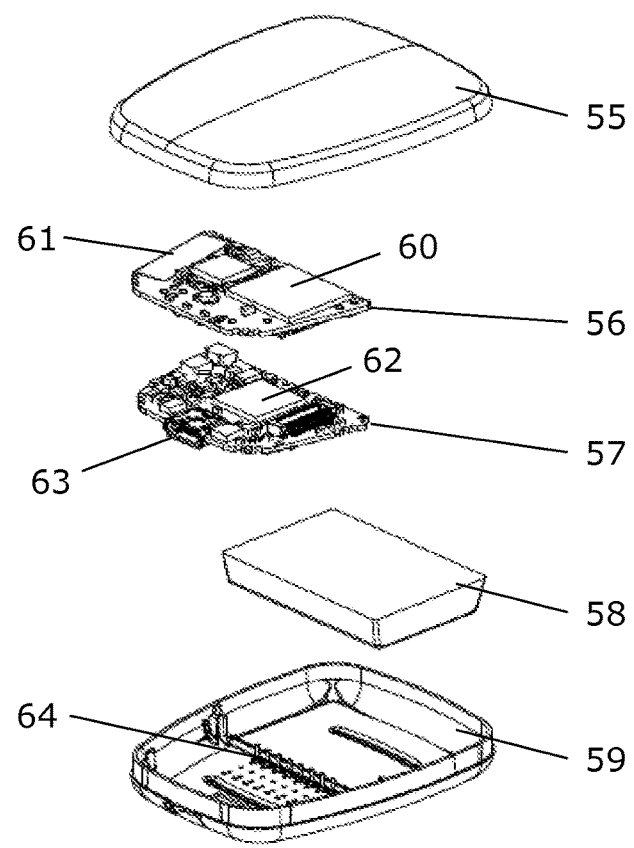
FIG. 13 illustrates an exploded view of the processor.
Figure 14:
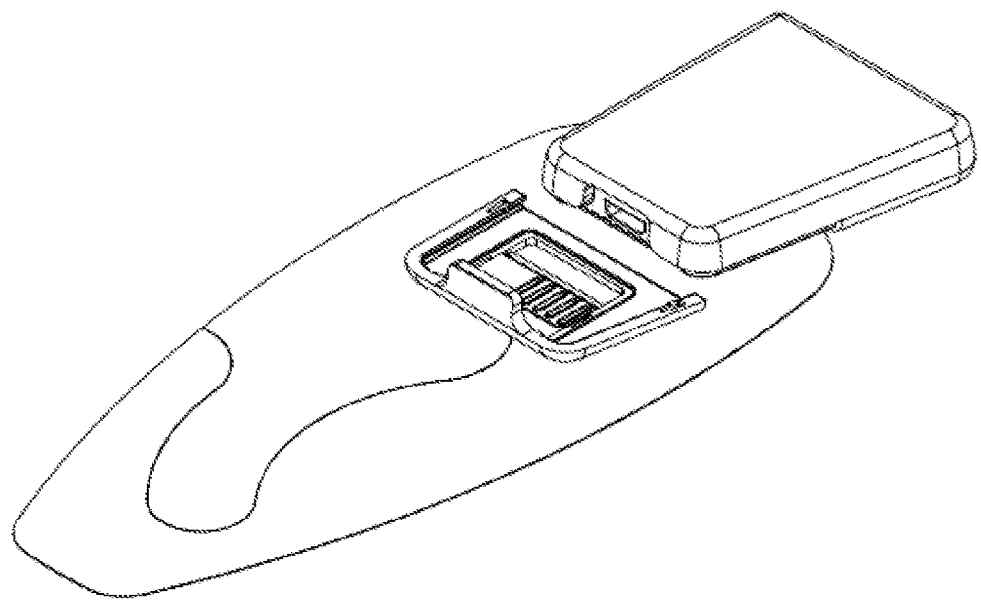
FIGS. 14 and 15 illustrate an embodiment where the processor is inserted sideways in a track.
Figure 15:
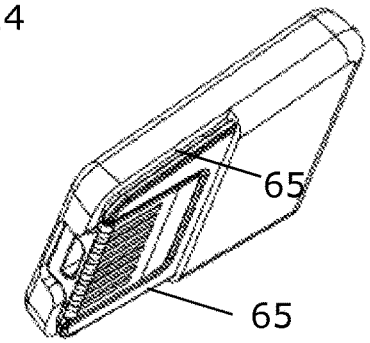
Figure 15:
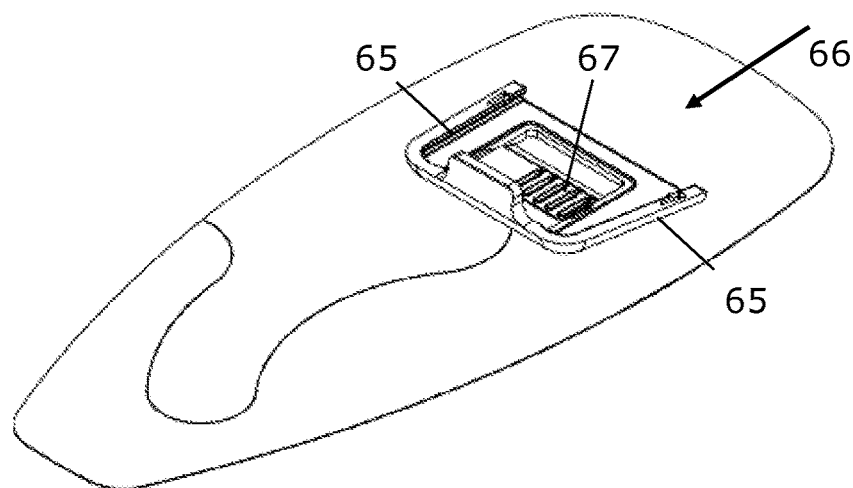

FIG. 13 illustrates an exploded view of the processor. The processor comprises a top-shell 55, two PCB (printed circuit boards) 56, 57, a battery 58 and a bottom shell 59 on which the top-shell is received to form a closed capsule. Internally, the processor comprises a memory block 60, an antenna 61 enabling wireless communication with an external data recipient, a CPU (computer processing unit) 62 programmed to perform processing of data received from or transmitted to the data collector. Additionally, the processor comprises a micro USB connector for connecting the processor to an external data receiver or for charging the battery. Additionally, the processor comprises a coupling 64 facing downwards and adapted for electrical connection to the coupling in the socket of the data collector.

Where the embodiment described above is adapted for insertion of the processor in a downwards direction from above into the socket, FIGS. 14 and 15 illustrate an embodiment where the processor is inserted sideways in a track formed by cooperating ledges 65 of the socket and processor. In this embodiment, the spring structure formed in the socket comprises protrusions separated by recesses or openings which are oblong and extend in a direction being parallel to the sideways direction indicated by arrow 66, and the first pattern 67 printed on the interface portion of the foldable sheet forms conductors which, correspondingly, extend in parallel with the sideways direction.

LISTED EMBODIMENTS

1. A monitoring device comprising a data collector and a separate processor, the data collector comprising a flexible foil attached to a less flexible socket, the foil forming a dermal side surface for adhesion of the data collector to a skin surface of a subject to be monitored and the socket forming a cavity for receiving the processor, wherein the data collector further comprises a foldable sheet with a first pattern of an electrically conductive material on an outer surface thereof, the first pattern extending between a sensing portion of the sheet which forms a layer in the flexible foil and an interface portion of the sheet which is folded into an aperture in the socket and forms an electrical coupling for electrically connecting the processor to the data collector.
2. A device according to embodiment 1, where the data collector further comprises at least one electrode for communicating an electrical signal between the monitoring device and the subject, and where the first pattern provides individual conductivity between each electrode and the coupling.
3. A device according to embodiment 2 or 3, where the at least one electrode comprises a second pattern of electrically conductive material on the outer surface of a sensing portion of the foldable sheet.
4. A device according to embodiment 3, where the second pattern and the first pattern are of identical electrically conductive material.
5. A device according to any of embodiments 3-4, where the socket is between the interface portion and the sensing portion of the sheet.
6. A device according to any of the preceding embodiments, comprising a spring structure forming part of the socket and located between the interface portion of the sheet and the dermal side surface of the data collector, the spring structure providing a spring force in an upwards direction being perpendicular to and directed away from the dermal side surface such that the force becomes towards the processor when the processor is received in the cavity.
7. A device according to any of the preceding embodiments, where the processor is receivable into the cavity in a downwards direction being perpendicularly to and directed towards the dermal side surface.
8. A device according to any of the preceding embodiments, where the processor is receivable into the cavity in a sideways direction being parallel to and directed towards the dermal side surface.
9. A device according to any of embodiment 6-9, where the spring structure comprises a number of upwards protrusions separated from adjacent protrusions by a recess or opening in the socket.
10. A device according to embodiments 8 and 9, where the recesses or openings between adjacent protrusions are oblong and extend in a direction being parallel to the sideways direction.
11. A device according to any of the preceding embodiments, where the socket forms a locking structure adapted to hold the processor in the cavity, the locking structure being adapted to apply a constant force on the processor in a downwards direction being perpendicularly to and directed towards the dermal side surface thereby forcing the processor into the cavity.
12. A device according to embodiment 11, where the locking structure is releasable by controlled destruction at a structurally weakened portion of the socket.
13. A monitoring device comprising a data collector and a separate processor, the data collector comprising a flexible foil attached to a less flexible socket, the foil forming a dermal side surface for adhesion of the data collector to a skin surface of a subject to be monitored and the socket forming a cavity for receiving the processor, wherein the processor comprises a connector for establishing a cabled connection to an external unit, the connector being covered by the socket, when the processor is received in the cavity.
14. A monitoring device comprising a data collector and a separate processor, the data collector comprising a flexible foil attached to a less flexible socket, the foil forming a dermal side surface for adhesion of the data collector to a skin surface of a subject to be monitored and the socket forming a cavity for receiving the processor, wherein the processor and the socket have matching non symmetric shapes facilitating the processor to be received in the cavity only in one singe orientation of the processor relative to the socket.
15. A method of making a device according to any of embodiments 1-14, the method comprising the steps of:
   providing an interface pattern of an electrically conductive material on an outer surface of a foldable sheet;
   providing a flexible foil which includes the foldable sheet and which forms a dermal side surface for adhesive contact with a skin surface;
   providing a socket which is less flexible than the foil;
   attaching the socket to an upper surface of the foil facing away from the dermal side surface; and
   folding an interface portion of the sheet through an aperture in the socket; and
   providing from the interface portion, a coupling for electrical communication with a matching coupling of the processor.

The invention claimed is:

1. A monitoring device comprising a data collector and a separate processor, wherein the data collector comprises a flexible foil attached to a less flexible socket, the foil forming a dermal side surface for adhesion of the data collector to a skin surface of a subject to be monitored and the socket forming a cavity for receiving the processor, wherein the data collector further comprises a foldable sheet with a first pattern of an electrically conductive material on an outer surface thereof, the first pattern extending between a sensing portion of the sheet which forms a layer in the flexible foil and an interface portion of the sheet which is folded into an aperture in the socket and forms an electrical coupling for electrically connecting the processor to the data collector, and wherein the processor is disposed within the cavity.

2. The device according to claim 1, wherein the data collector further comprises at least one electrode for communicating an electrical signal between the monitoring device and the subject, and where the first pattern provides individual conductivity between each electrode and the coupling.

3. The device according to claim 2, wherein the at least one electrode comprises a second pattern of electrically conductive material on the outer surface of the sensing portion of the foldable sheet.

4. The device according to claim 3, wherein the second pattern and the first pattern are of identical electrically conductive material.

5. The device according to claim 3, wherein the socket is between the interface portion and the sensing portion of the sheet.

6. The device according to claim 1, wherein the device comprising a spring structure forming part of the socket and located between the interface portion of the sheet and the dermal side surface of the data collector, the spring structure providing a spring force in an upwards direction being perpendicular to and directed away from the dermal side surface such that the force becomes towards the processor when the processor is received in the cavity.

7. The device according to claim 1, wherein the processor is received into the cavity in a downwards direction being perpendicular to and directed towards the dermal side surface.

8. The device according to claim 1, wherein the processor is received into the cavity in a sideways direction being parallel to and directed towards the dermal side surface.

9. The device according to claim 6, wherein the spring structure comprises a number of upwards protrusions separated from adjacent protrusions by recesses or openings in the socket.

10. The device according to claim 9, wherein the processor is received into the cavity in a sideways direction being parallel to and directed towards the dermal side surface, and wherein the recesses or openings between adjacent protrusions are oblong and extend in a direction being parallel to the sideways direction.

11. The device according to claim 1, wherein the socket forms a locking structure adapted to hold the processor in the cavity, the locking structure being adapted to apply a constant force on the processor in a downwards direction being perpendicular to and directed towards the dermal side surface thereby forcing the processor into the cavity.

12. The device according to claim 11, wherein the socket comprises a structurally weakened portion, and the locking structure is releasable by controlled destruction at the structurally weakened portion of the socket.

13. The monitoring device according to claim 1, wherein the processor comprises a connector for establishing a cabled connection to an external unit, the connector being covered by the socket, when the processor is received in the cavity.

14. The monitoring device according to claim 1, wherein the processor and the socket have matching non symmetric shapes facilitating the processor to be received in the cavity only in one singe orientation of the processor relative to the socket.

15. A method of making a device according to claim 1, wherein the method comprising the steps of:
- providing the first pattern of the electrically conductive material on the outer surface of the foldable sheet;
- providing the flexible foil which includes the foldable sheet and which forms the dermal side surface for adhesive contact with the skin surface;
- providing the socket which is less flexible than the foil;
- attaching the socket to an upper surface of the foil facing away from the dermal side surface; and
- folding the interface portion of the sheet through the aperture in the socket;
- providing, from the interface portion, the coupling for electrical communication with a matching coupling of the processor; and
- coupling the coupling of the processor to the coupling of the interface portion.

* * * * *